United States Patent

Langer et al.

Patent Number: 6,043,395
Date of Patent: Mar. 28, 2000

[54] PROCESS FOR PREPARING VARIABLE MIXTURES OF CYCLOHEXYL-AMINE AND DICYCLOHEXYLAMINE

[75] Inventors: Reinhard Langer, Tönisvorst; Gerd-Michael Petruck, Erkrath, both of Germany

[73] Assignee: Bayer Aktiengesellschaft, Leverkusen, Germany

[21] Appl. No.: 09/323,793

[22] Filed: Jun. 1, 1999

[30] Foreign Application Priority Data

Jun. 4, 1998 [DE] Germany ............ 198 24 906

[51] Int. Cl.$^7$ .................. C07C 209/00
[52] U.S. Cl. .......... 564/450; 502/170; 502/104; 502/111
[58] Field of Search ............ 564/450; 502/170, 502/104, 111

[56] References Cited

U.S. PATENT DOCUMENTS

| | | | |
|---|---|---|---|
| 3,363,108 | 1/1968 | Brake | 260/563 D |
| 3,636,108 | 1/1972 | Brake | 260/563 D |
| 4,049,584 | 9/1977 | Weissel | 252/470 |
| 4,729,977 | 3/1988 | Immel et al. | 502/170 |
| 4,960,941 | 10/1990 | Vedage et al. | 564/450 |
| 5,023,226 | 6/1991 | Immel et al. | 502/313 |
| 5,248,840 | 9/1993 | Immel et al. | 568/747 |
| 5,322,965 | 6/1994 | Immel et al. | 564/446 |
| 5,360,934 | 11/1994 | Vedage et al. | 564/451 |
| 5,386,060 | 1/1995 | Immel et al. | 564/450 |
| 5,773,657 | 6/1998 | Rütter et al. | 564/450 |

FOREIGN PATENT DOCUMENTS

| | | |
|---|---|---|
| 0 053 818 | 5/1985 | European Pat. Off. . |
| 0 560 127 | 5/1996 | European Pat. Off. . |
| 1530477 | 6/1968 | France . |
| 805518 | 5/1951 | Germany . |
| 1106319 | 5/1961 | Germany . |
| 43-03180 | 2/1968 | Japan . |
| 969542 | 9/1964 | United Kingdom . |

*Primary Examiner*—Paul J. Killos
*Attorney, Agent, or Firm*—Joseph C. Gil; Diderico van Eyl

[57] ABSTRACT

A high-pressure process for hydrogenating aromatic amines to give mixtures of the corresponding cycloaliphatic amines and dicycloaliphatic amines in variable ratios in the presence of rhodium catalysts.

21 Claims, No Drawings

PROCESS FOR PREPARING VARIABLE MIXTURES OF CYCLOHEXYL-AMINE AND DICYCLOHEXYLAMINE

BACKGROUND OF THE INVENTION

The present invention relates to a high-pressure process for hydrogenating aromatic amines to give mixtures of the corresponding cycloaliphatic amines and dicycloaliphatic amines in variable ratios in the presence of rhodium catalysts which may, if desired, be modified with a noble metal selected from among iridium (Ir), ruthenium (Ru), osmium (Os), palladium (Pd) or platinum (Pt) or a mixture of these metals on supports modified with oxides of chromium (Cr), molybdenum (Mo), tungsten (W), manganese (Mn) or rhenium (Re) or a mixture of these oxides.

Substituted and unsubstituted cyclohexylamines and dicyclohexylamines are used for preparing ageing inhibitors for rubbers and plastics, as corrosion inhibitors in aqueous solution and as intermediates for textile auxiliaries and crop protection agents.

It is known that cyclohexylamine can be prepared by pressure hydrogenation of aniline. For this hydrogenation, use is made mainly of noble metal catalysts, for example an Ru catalyst modified with alkali metal as described in U.S. Pat. Nos. 3,636,108, additionally using $NH_3$ and, if desired, a solvent. A further process for the pressure hydrogenation of aniline to give cyclohexylamine is described in DE-B 1,106,319, where an Ru catalyst is likewise used. In this process, dicyclohexylamine formed together with the cyclohexylamine is added back to the starting material. However, because of the simultaneous formation of cyclohexane, the process gives only a moderate yield. According to EP-B 0,053,818, supported Pd catalysts are better than Ru catalysts; the catalysts described there contain additives which either come from a group of basic compounds of the alkali metals, alkaline earth metals and rare earth metals or a group comprising the metals Fe, Ni, Co, Mn, Zn, Cd and Ag. These catalysts allow the reduction of substituted anilines to form the corresponding cyclohexylamines, but the corresponding dicyclohexyl-amines are missing entirely. The same applies to Co catalysts which contain a basic additive (GB 969 542) and to Raney Co (JP 68/03 180).

In the processes described for the pressure hydrogenation of aniline, the dicyclohexylamine is formed only as a by-product, if at all, in addition to the cyclohexylamine. To obtain dicyclohexylamine in larger amounts, it is prepared by separate processes. Thus, for example, it can be obtained by pressure hydrogenation of diphenylamine using an $Ru/Al_2O_3$ catalyst (DE-B 1,106,319). Furthermore, dicyclohexylamine is formed in the reaction of cyclohexanone with cyclohexylamine under a hydrogen pressure of 4 bar in the presence of Pd on carbon (FR 1,530,477).

U.S. Pat. No. 5,360,934 discloses an improved hydrogenation process in which aromatic amines are hydrogenated to their ring hydrogenated counterparts. The improvement of the process resides in the utilization of a catalyst comprising rhodium carried on a support of kappa, theta or delta alumina. U.S. Pat. No. 4,960,941 discloses an improved hydrogenation process in which aromatic amines are hydrogenated to their ring hydrogenated counterparts. The improvement of the process resides in the utilization of a catalyst comprising rhodium carried on titania support. U.S. Pat. No. 5,773,657 discloses the hydrogenation of aromatic compounds in which at least one amino group is bonded to an aromatic nucleus. The process teaches pressures above 50, preferably from 150 to 300 bar. U.S. Pat. No. 5,023,226 relates to rutheninum catalysts also containing palladium, platinum in addition to ruthenium on a support treated with chromium and manganese from the group consisting of $Al_2O_3$ and aluminum spinel.

EP-A 0,501,265 discloses a process for preparing substituted or unsubstituted cyclohexylamine and substituted or unsubstituted dicyclohexylamine by catalytic hydrogenation of substituted or unsubstituted aniline using a catalyst containing Ru, Pd or a mixture of both metals applied to a support comprising niobic acid or tantalic acid or a mixture of the two. EP-A 503,347 discloses a further process for preparing substituted or unsubstituted cyclohexylamine and substituted or unsubstituted dicyclohexylamine by hydrogenation of a corresponding substituted aniline using a catalyst prepared by treating an α- or γ-$Al_2O_3$ as support first with at least one compound of rare earth metals and at least one compound of manganese and then with at least one Pd compound.

However, all the catalysts and processes mentioned still have disadvantages in respect of conversion, selectivity, operating life of the catalyst, the necessity of additionally using $NH_3$, etc. A serious problem in catalyst beds for the continuous trickling-phase hydrogenation is the tendency of all previously known Ru-containing catalysts to catalyze deaminations and hydrogenolysis of the molecules to form methane as the temperatures rise. The intrinsically exothermic hydrogenation can thus, for example in the case of slight deviations from a given temperature, change over, first slightly then possibly very rapidly, into the far more strongly exothermic methanization and lead to a situation which can no longer be controlled, even as far as explosions. For this reason, very comprehensive and reliable safety precautions have to be undertaken when using Ru-containing catalysts. However, this makes the suitability of these catalysts for industrial plants questionable.

The problems which still occur today despite the progress made are shown by EP-A 0,560,127 filed in 1992: although the Ru-Pd catalysts on alkaline supports which are used here can hydrogenate aromatic amines at low pressure, they can be subjected only to low velocities of from 0.03 to 0.05 g/ml of catalyst and hour, which requires large amounts of catalyst and large reactors; $NH_3$ has to be added in large amounts and the temperatures are held in the vicinity of 160° C. Even so, hydrogenolysis, which can be recognized by the formation of benzene and cyclohexane, still always occurs despite the fact that conversion continues to be incomplete; the selectivity leaves something to be desired and the operating life of the catalysts is significantly less than, for example, in EP-A 0,324,983. Incipient deactivation of the catalyst is indicated by the slowly decreasing conversion.

It is therefore an object of the invention to provide catalysts for the industrial hydrogenation of aromatic amines to give cycloaliphatic amines, which catalysts effect complete conversion at high velocities, have a high selectivity in respect of the formation of primary and secondary cycloaliphatic amines, possess a long life and, in particular, no longer cause hydrogenolysis and methanization of the substrates.

In one complicated process, dicyclohexylamine can be obtained from the hydrogenation product of aniline over a Ni catalyst by fractional condensation. Part of the ammonia which is also formed is removed from the remaining mixture and the remainder is recirculated to the reaction (DE-C 805,518).

EP-A 0,208,933 describes Rh catalysts on supports modified with Cr-Mn salts. The catalysts were developed for dehydrogenating intermediates for o-phenylphenol formation at high temperatures.

EP-A 0,535,482 likewise describes high-temperature-resistant Rh catalysts on supports modified with Cr-Mn salts for the preparation of o-phenylphenol. The catalysts contain further noble metals in addition to the Rh. The Rh catalysts can be used in thermostatted, static catalyst beds for dehydrogenation at low pressures and at temperatures of from 300 to 400° C.

It has surprisingly been found that catalysts containing Rh on specifically treated support materials are potent catalysts for achieving a process for the pressure hydrogenation of anilines, which catalysts display no tendency to catalyze the strongly exothermic hydrogenolysis to form methane, even at high temperatures and pressures, and thus ensure a high level of production safety.

SUMMARY OF THE INVENTION

The invention provides a process for hydrogenating aromatic amines to give mixtures of cycloaliphatic amines and dicycloaliphatic amines at pressures of from 50 to 500 bar over base-treated supported noble metal catalysts, characterized in that the support material has been laden with salts of Cr, Mo, W, Mn or Re or a mixture of such salts and that the resulting support material has been activated with Rh as noble metal and, if desired Ir, Ru, Os, Pd and/or Pt as additional noble metal component.

DETAILED DESCRIPTION OF THE INVENTION

Suitable starting compounds for the process of the invention are aromatic amines as described, for example, in German Auslegesch-rift 2,502,894 and U.S. Pat. No. 3,636,108. Preference is given to aniline, $C_1$–$C_6$-alkylanilines alkylated either on the ring or on the nitrogen, $C_1$–$C_6$-alkylated diaminobenzenes, aminonaphthalenes and $C_1$–$C_3$-alkylated amino-naphthalenes, diaminonaphthalenes and diamino-diphenyl-$C_1$–$C_3$-alkanes.

Examples which may be mentioned are aniline, N-methylaniline, N-ethylaniline, N,N-dimethylaniline, N,N-diethylaniline, N-ethyltoluidine, N-cyclohexylaniline, N-cyclohexylideneaniline, o-, m-, p-toluidine, 2,4-, 2,6-, 2,3-diamino-toluene, diphenylamine, 1- and 2-aminonaphthalene, 1,4-, 1,5-, 2,5-, 2,6-, 2,7-diaminonaphthalene and the isomeric diaminophenyl-methanes.

Preferred examples are aniline, N-methylaniline, N-ethylaniline, N,N-dimethylaniline, N,N-diethylaniline, N-cyclohexylaniline, N-cyclohexyl-ideneaniline, o-, m-, p-toluidine, 2,4-, 2,6-, 2,3-diamino-toluene, diphenylamine.

Particularly preferred examples are aniline, 2,4- and 2,6-diamino-toluene.

The process of the invention is particularly preferably used for hydrogenating aniline.

The supported noble metal catalysts for the process of the invention comprise support material which has been laden with salts of the metals Cr, Mo, W, Mn or Re or a mixture of such salts; the supported noble metal catalysts further comprise Rh as noble metal and, if desired, an additional noble metal component selected from among Ir, Ru, Os, Pd and/or Pt.

Suitable support materials are, for example aluminas, $Al_2O_3$ in its various modifications ($\alpha$, $\kappa$, $\eta$, $\gamma$), also support materials otherwise customary for noble metals, e.g. $TiO_2$, kieselguhr, silica gel, $BaCO_3$, $CaCO_3$, ZnO, MgO, pumice, $ZrO_2$, activated carbon and the oxides or hydrated oxides of Cr, Mo, W, Mn and/or Re. Preferred support materials are $TiO_2$, $BaCO_3$, MgO, particularly preferably $\gamma$-$Al_2O_3$ and the oxides or hydrated oxides of Cr, Mo, W, Mn and/or Re, very particularly preferably $\gamma$-$Al_2O_3$.

The support material can be used as powder or in pelletized form as spheres or as extrudates such as rings, wagon wheels, etc. It is also possible to use shaped bodies such as honeycomb bodies or cross-channel structures.

Preference is given to using a support material having a high BET surface area. The BET surface area should be above 50 $m^2$/g, preferably from 100 to 500 $m^2$/g, particularly preferably from 200 to 400 $m^2$/g.

If the support material contains oxides or hydrated oxides of Cr, Mo, W, Mn or Re or a mixture of such oxides or hydrated oxides, it may be possible to omit the modification of the support material described below before application of the noble metal components.

If a support material which is free of Cr, Mo, W, Mn or Re is used, it first needs to be laden with one or more of these components. This can be achieved, for example, by impregnation or spraying of the support material with suitable salts of these elements. By means of drying and then heating at temperatures of from about 200 to 450° C., the salts applied are converted into compounds which adhere to the support material. However, the application of the compounds of Cr, Mo, W, Mn and/or Re can also be achieved by coprecipitation of oxide/hydroxide mixtures on the impregnated support material using alkali metal, alkaline earth metal or ammonium hydroxides and, if desired, subsequent washing out of soluble components using water.

Particular preference is given to uniform precipitation by slow release of the base by hydrolysis of a less basic precursor; ureas and urethanes are particularly suitable for this purpose. Urea is very particularly useful.

The support material which has been pretreated in this way is dried and then heated for from 10 minutes to 10 hours at from 200 to 450° C., preferably from 250 to 430° C., with the temperature also being able to be increased in steps within this range.

Suitable salts of Cr, Mo, W, Mn and Re are, for example, the acetates, nitrates, halides or sulphates. Likewise suitable are the water-soluble oxides of the higher oxidation states, particularly the ammonium salts of Cr, Mo, W, Mn and Re oxides.

Preference is given to using support materials which have been pretreated with Cr and/or Mn salts.

After any washing out of soluble compounds and drying and heating the support material modified with Cr, Mo, W, Mn and/or Re, the support material is ready for application of the other active substances.

The other active substances are Rh and alkali metal hydroxide or alkaline earth metal hydroxide, if desired, Ir, Ru, Os, Pd and/or Pt and, if desired, alkali metal sulphate or alkaline earth metal sulphate. The noble metals are applied in the form of solutions of their salts, for example in water. Suitable salts are, for example, the halides, preferably the chlorides, acetates, nitrates and acetylacetonates. A suitable alkali metal hydroxide is, for example, NaOH or KOH; an example of a suitable alkaline earth metal hydroxide is $Mg(OH)_2$.

An example of a sulphate component is $K_2SO_4$. The compounds can be applied individually or together by impregnation or spraying. A drying step is carried out between each impregnation step.

Preference is given to applying first Rh, then, if desired, the noble metals for modification, followed by the alkali metal hydroxide and, if desired, the alkali metal sulphate and, if desired, a further impregnation with base.

After each impregnation with noble metal, a reduction may, if desired, be carried out using, for example, hydrogen or another reducing agent. In any case, a reduction using, for example, hydrogen at temperatures of from 80 to 350° C. is carried out at the end of the last drying step.

The finished supported noble metal catalyst contains from 0.1 to 10% by weight, preferably from 0.3 to 3% by weight, of noble metal of which from 100 to 30%, preferably from 100 to 70%, is Rh; the remaining noble metal consists of Ir, Ru, Os, Pd and/or Pt. The supported noble metal catalyst also contains from 0.05 to 5% by weight of Cr, Mo, W, Mn and/or Re, preferably Cr and/or Mn, plus from 0.05 to 15% by weight of alkali metal or alkaline earth metal ions and, if desired, from 0.05 to 3% by weight of sulphur in the form of compounds.

In the process of the invention, preference is given to using a suitable supported noble metal catalyst in pelletized form as fixed beds. The beds can be operated without removal of heat or be thermostatted using tube bundles through or around which heat-transfer medium flows. Likewise advantageous is a combination of thermostatted and adiabetic beds or a sequence of adiabatic reactors with coolers arranged in between. The design of suitable reactors for such beds is prior art and known to those skilled in the art.

The reaction can be carried out by heating aromatic amine and hydrogen, if desired together with compounds to be recycled, e.g. hydrogen, ammonia, N-cyclohexylaniline, passing the heated mixture over the catalyst, condensing part of the condensable compounds by cooling and discharging this part together with the liquid phase, bleeding off part of the remaining gas stream to remove inert compounds from the system and returning the remainder to the reaction via compression.

The process of the invention is carried out, for example, at temperatures of from 100 to 400° C., preferably from 150 to 350° C., particularly preferably from 170 to 330° C.

The reaction is carried out in a pressure range from 50 to 500 bar, preferably from 100 to 400 bar, particularly preferably from 200 to 300 bar.

The aromatic amine to be reacted is reacted, for example, with hydrogen in a molar ratio of from 1:500 to 1:5, preferably from 1:200 to 1:10, particularly preferably from 1:150 to 1:40.

Small amounts of ammonia can be passed over the catalyst together with the aromatic amines and the hydrogen.

The space velocity over the catalysts in the process of the invention is, for example, from 0.05 to 5 kg, preferably from 0.2 to 2 kg, of aniline per liter of catalyst and hour.

The selectivities in respect of cyclohexylamine and dicyclohexyl-amine in the process of the invention are significantly above 90%; they are above 98% at below 300° C. and above 99% at below 250° C.

The ratio of monocyclohexylamine and dicyclohexylamine varies from 20:1 to 0.8:1, depending on the amount of base with which the catalyst has been after-treated, the reaction temperature and the ammonia content of the feed mixture.

The process of the invention makes it possible to convert aromatic amines flexibly into mixtures of monocyclohexylamine and dicyclohexyl-amine; a high space velocity over the catalyst is possible and the reaction is thermally safe to carry out because of high selectivities even at high temperatures!

The invention is further illustrated but is not intended to be limited by the following examples in which all parts and percentages are by weight unless otherwise specified.

EXAMPLES

Example 1 (catalyst preparation)

1 l of γ-$Al_2O_3$ from Rhone-Poulenc (SPH 501, spheres, diam.=4–6 mm, BET surface area about 350 $m^2/g$) were impregnated with 320 ml of a solution of 30.1 g of $MnSO_4 \times H_2O$, 22.3 g of $(NH_4)_2Cr_2O_7$ and 164 g of urea. The impregnated support was kept in motion in a saturated steam atmosphere for 1 hour at 90° C. This was followed by washing twice with 160 ml each time of water to remove soluble compounds. The support obtained in this way was dried and subsequently heated for 30 minutes at 300° C. in a rotating drum.

20.3 g of $RhCl_3$ in 360 ml of water were applied by impregnation and the catalyst precursor was subsequently dried at 110° C.

320 ml of a solution of 24 g of NaOH and 24 g of $K_2SO_4$ in water were then applied, the precursor was dried and again impregnated with 50 g of NaOH in 320 ml of water.

The catalyst was dried and activated in a stream of hydrogen for 3.5 hours at 160° C.

The finished catalyst contained 8 g of Rh, 9.2 g of Cr, 9.8 g of Mn, 74 g of NaOH and 24 g of $K_2SO_4$ per liter.

Example 2

50 ml of catalyst from Example 1 were introduced into a pressure-resistant tube reactor having an internal diameter of 1.8 cm to produce a bed having a height of 30.5 cm. The reactor was heated by means of oil and was operated at a hydrogen pressure of 270 bar. Before commencement of the reaction, the catalyst was activated in a stream of hydrogen for 21 hours at 141° C. under superatmospheric pressure.

The table below shows the composition of the product mixture at a space velocity of 1 g of aniline per 1 of catalyst and hour and a molar ratio of hydrogen to aniline of 90/1.

The catalyst was operated for 2,000 hours without signs of deactivation and the test was then stopped.

Table: Hydrogenation of aniline under superatmospheric pressure, without methane formation even at high temperatures

| Temp. ° C. | CHA/ DCA | CHA % | DCA % | ANI % | Bz % | CYOL % | Remainder % | $CH_4$ vpm |
|---|---|---|---|---|---|---|---|---|
| 180 | 13.4 | 91.2 | 6.8 | 1.46 | 0.06 | 0.28 | 0.20 | 0 |
| 220 | 9.03 | 89.4 | 9.9 | 0 | 0.13 | 0.30 | 0.27 | 0 |
| 300 | 1.14 | 52.0 | 45.6 | 0 | 1.89 | 0.25 | 0.26 | 5 |
| 330 | 1.36 | 52.5 | 38.6 | 0 | 8.07 | 0.27 | 0.56 | 12 |

The column headings have the following meanings, from left to right:
Temperature of the thermostatted oil circuit and the starting materials in °C.,
Weight ratio of cyclohexylamine (CHA) to dicyclohexylamine (DCA) in the liquid (liq.) product,
Percent by weight cyclohexylamine in the liq. product,
Percent by weight of dicyclohexylamine in the liq. product,
Percent by weight of unreacted aniline (ANI) in the liq. product,
Percent by weight of benzene (Bz) in the liq. product,
Percent by weight of cyclohexanol (CYOL) in the liq. product,
Percent by weight of the sum of the remaining compounds in the liq. product,
Parts by volume of methane per 1 million parts by volume of waste gas.
Cyclohexanol is formed because of small amounts of water in the hydrogen gas.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for hydrogenating aromatic amines to into a mixture of cycloaliphatic amines and dicycloaliphatic amines in variable ratios at pressures of from 50 to 500 bar comprising hydrogenating aromatic amines over base-treated supported noble metal catalysts, wherein the support material of the supported noble metal catalyst has been treated with a metal component selected from the group consisting of chromium salts, molybdenum salts, tungsten salts, manganese salts, rhenium salts, mixtures thereof, and wherein the support material is activated with rhodium.

2. Process according to claim 1, wherein the support material is further activated with a component comprising a component selected from the group consisting of iridium, ruthenium, osmium, palladium and platinum.

3. Process according to claim 1, wherein the supported noble metal catalyst used contains from 0.1 to 10% by weight of a noble metal.

4. Process according to claim 3, wherein the supported noble metal catalyst comprises rhodium in an amount from 100 to 30% of the 0.1 to 10% by weight of the noble metal content.

5. Process according to claim 1, wherein the supported noble metal catalyst contains from 0.05 to 5% by weight of a component selected from the group consisting of chromium, molydenum, tungsten, manganese, and rhenium, and from 0.05 to 15% by weight of alkali metal or alkaline earth metal ions.

6. The process of claim 5, wherein the supported noble metal catalyst further contains from 0.05 to 3% by weight of sulphur in the form of compounds.

7. Process according to claim 1, wherein the supported noble metal catalyst contains from 0.05 to 5% by weight of a component selected from the group consisting of chromium and magnesium.

8. Process according to claim 1, wherein the reaction is carried out at a temperature ranging from about 100 to 400° C.

9. Process according to claim 1, wherein aromatic amines used comprise an aromatic amine component comprising a component selected from the group consisting of aniline, $C_1$–$C_6$-alkylanilines alkylated either on the ring or on the nitrogen, $C_1$–$C_6$-alkylated diaminobenzenes, aminonaphthalenes, $C_1$–$C_3$-alkylated aminonaphthalenes, diaminonaphthalenes and diamino-diphenyl-$C_1$–$C_3$-alkanes.

10. Process according to claim 1, wherein the support material comprises a component selected from the group consisting of aluminas, $TiO_2$, kieselguhr, silica gel, $BaCO_3$, $CaCO_3$, ZnO, MgO, pumice, $ZrO_2$, activated carbon, chromium oxides, molydenum oxides, tungsten oxides, manganese oxides, rhenium oxides, chromium hydrated oxides, molydenum hydrated oxides, tungsten hydrated oxides, manganese hydrated oxides, rhenium hydrated oxides.

11. Process according to claim 10, wherein the support material is used as powder or in pelletized form as spheres or as extrudates such as rings, wagon wheels or shaped bodies.

12. Process for preparing supported noble metal catalysts which contain chromium, molybdenum, tungsten, manganese or rhenium, comprising the steps:

(a) treating a support material with a metal component comprising a component selected from the group consisting of chromium salts, molybdenum salts, tungsten salts, manganese salts and rhenium salts;

(b) drying and heating at temperatures of from about 200 to 450° C.;

(c) washing out soluble compounds;

(d) treating the support material with rhodium;

(e) treating the support material with a hydroxide component selected from the group of alkali metal hydroxides and alkaline earth metal hydroxides; and (f) drying and reducing with hydrogen at temperatures of from 80 to 350° C.

13. The process of claim 12, wherein the step (a) of treating comprises spraying the support with the metal component.

14. The process of claim 12, wherein the step (a) of treating comprises impregnating the support with the metal component.

15. The process of claim 12, wherein in step (d) the support material is further treated with a component selected from the group consisting of iridium, ruthenium, osmium, palladium and platinum.

16. The process of claim 12, wherein in step (e) the support material is further treated with a component selected from the group consisting of alkali metal sulphates and alkaline earth metal sulphates.

17. A catalyst support made by a process comprising the steps of:

(a) treating a support material with a metal component comprising a component selected from the group consisting of chromium salts, molybdenum salts, tungsten salts, manganese salts, and rhenium salts;

(b) drying and heating at temperatures of from about 200 to 450° C.;

(c) washing out soluble compounds;

(d) treating the support material with rhodium;

(e) treating the support material with a hydroxide component selected from the group of alkali metal hydroxides and alkaline earth metal hydroxides; and (f) drying and reducing the support with hydrogen at temperatures of from 80 to 350° C.

18. The process of claim 17, wherein the step (a) of treating comprises spraying the support with the metal component.

19. The process of claim 17, wherein the step (a) of treating comprises impregnating the support with the metal component.

20. The process of claim 17, wherein in step (d) the support material is further treated with a component selected from the group consisting of iridium, ruthenium, osmium, palladium and platinum.

21. The process of claim 17, wherein in step (e) the support material is further treated with a component selected from the group consisting of alkali metal sulphates and alkaline earth metal sulphates.

* * * * *